(12) United States Patent
Doms et al.

(10) Patent No.: US 9,433,039 B2
(45) Date of Patent: Aug. 30, 2016

(54) METHOD AND APPARATUS FOR HEATING VOLUMES OF MEDIA IN A CLOSED RECEPTACLE BY MEANS OF AN ELECTROMAGNETIC RADIATION

(71) Applicants: ASKION GmbH, Gera (DE); GERALD WAGNER CONSULTING LLC, Upper Grandview, NY (US)

(72) Inventors: Lutz Doms, Poehl (DE); Gerald Wagner, Upper Grandview, NY (US)

(73) Assignees: ASKION GMBH, Gera (DE); GERALD WAGNER CONSULTING LLC, Upper Grandview, NY (US)

( * ) Notice: Subject to any disclaimer, the term of this patent is extended or adjusted under 35 U.S.C. 154(b) by 0 days.

(21) Appl. No.: 14/559,054

(22) Filed: Dec. 3, 2014

(65) Prior Publication Data
US 2015/0173130 A1  Jun. 18, 2015

(30) Foreign Application Priority Data

Dec. 16, 2013 (DE) .................. 10 2013 114 101

(51) Int. Cl.
| | |
|---|---|
| A61L 2/04 | (2006.01) |
| H05B 6/68 | (2006.01) |
| A61L 2/00 | (2006.01) |
| A61L 2/12 | (2006.01) |
| H05B 6/64 | (2006.01) |
| A61M 5/44 | (2006.01) |

(52) U.S. Cl.
CPC .............. *H05B 6/68* (2013.01); *A61L 2/0064* (2013.01); *A61L 2/04* (2013.01); *A61L 2/12* (2013.01); *A61M 5/44* (2013.01); *H05B 6/645* (2013.01); *A61L 2202/23* (2013.01)

(58) Field of Classification Search
CPC ...................................................... A61L 2/0029
USPC ............................................................ 422/21
See application file for complete search history.

(56) References Cited

U.S. PATENT DOCUMENTS

| | | | |
|---|---|---|---|
| 8,668,883 B2 | 3/2014 | Garner | |
| 9,089,623 B2* | 7/2015 | Michalik | ................... A61L 2/20 |
| 2006/0163169 A1* | 7/2006 | Eckhardt | ................ C02F 1/002 |
| | | | 210/748.11 |
| 2010/0047116 A1 | 2/2010 | Garner | |
| 2010/0178196 A1 | 7/2010 | Garner | |
| 2013/0315785 A1 | 11/2013 | Michalik | |
| 2014/0116961 A1 | 5/2014 | Bokermann et al. | |
| 2014/0190519 A1 | 7/2014 | Simundic et al. | |
| 2014/0322833 A1* | 10/2014 | Yamaguchi | ......... H01J 37/3045 |
| | | | 438/14 |

FOREIGN PATENT DOCUMENTS

| | | |
|---|---|---|
| DE | 102011102687 A1 | 11/2012 |
| WO | 2013037723 A1 | 3/2013 |

OTHER PUBLICATIONS

Fessia et al. "Moist Heat Intraluminal Disinfection of CAPD Connectors", Perit. Dial. Bull. 6, 1990, pp. 164-168.

(Continued)

*Primary Examiner* — Sean E Conley
(74) *Attorney, Agent, or Firm* — Abel Law Group, LLP

(57) ABSTRACT

The invention relates to a method for heating volumes of media (11) in a closed receptacle (10) by means of an electromagnetic radiation (2), wherein a database (4) is prepared based on measurements of reference receptacles, and irradiation regimes are selected or generated using the database (4) and used for heating the media (11). The invention further relates to an apparatus for carrying out the method.

14 Claims, 5 Drawing Sheets

(56) References Cited

OTHER PUBLICATIONS

Grabowy et al. "New Connection Method for Isolating and Disinfecting Intraluminal Path During Peritoneal Dialysis Solution-Exchange Procedures", Adv. Perit. Dial. 14, 1998, pp. 149-153.

Carr et al.: "Sterile docking using microwave heating", Microwave Symposium Digest, 1992., IEEE MTT- S International Albuquerque, NM USA Jun. 1, 1992, pp. 1267-1270.

* cited by examiner

METHOD AND APPARATUS FOR HEATING VOLUMES OF MEDIA IN A CLOSED RECEPTACLE BY MEANS OF AN ELECTROMAGNETIC RADIATION

CROSS-REFERENCE TO RELATED APPLICATIONS

The present application claims priority under 35 U.S.C. §119 of German Patent Application No. 102013114101.3, filed Dec. 16, 2013, the entire disclosure of which is expressly incorporated by reference herein.

BACKGROUND OF THE INVENTION

1. Field of the Invention

The invention is directed to a method and apparatus for heating volumes of media in a closed receptacle by means of an electromagnetic radiation.

2. Discussion of Background Information

In medical applications and therapeutic procedures, it is often necessary to provide a patient with a permanent access. The patient can then receive solutions with medication or other contents, as needed, via this access.

A typical application is for dialysis patients who must occasionally be connected to a dialysis machine. In this regard, it is possible to provide a coupling device at the permanent access remaining on the patient so that the access can be connected to a dialysis machine.

Of course, it is extremely important that the risk of infecting the patient be eliminated as far as possible when reconnecting the coupling device.

A method for disinfecting coupling devices of this type is described in a publication by Fessia et al. (1990, Moist heat intraluminal disinfection of CAPD connectors, Perit.Dial-.Bull. 6: 164-168). The coupling devices usually comprise two parts having connection areas that correspond to one another. This system is also known as a Luer® Lock or Luer® connector (ISO 594-1: 1986; EN 20594-1:1993; DIN EN 20594-1:1996). In closed condition, the coupling device has an interior space through which, e.g., the dialysis solution flows. In order to disinfect the coupling device before a treatment, this coupling device is filled with the dialysis solution (hereinafter referred to as medium) and the infusion line and diffusion line for the dialysis solution are closed. Subsequently, the coupling device is irradiated by microwave radiation until the medium reaches a temperature of at least 100° C. The irradiation period specified by Fessia et al. is 54 seconds. It was possible by means of this method to reduce the 106 microorganisms tested (gram positive and gram negative bacteria, yeasts and mold) to the point where the disinfection requirements (bacterial count reduced by at least a factor of $10^5$) were met.

Grabowy et al. (1998, New connection method for isolating and disinfecting intraluminal path during peritoneal dialysis solution-exchange procedures, Adv.Perit.Dial. 14:149-154) describe a coupling device for a dialysis machine having infusion line and diffusion line closed in a pressure-tight manner and the medium is heated by microwave radiation. The medium is heated from 25° C. to temperatures of greater than 100° C. within about 10 seconds, which is made possible by the pressure-tight closure. The closure further prevents escape of potentially contaminated parts of the medium and ensures that all of the potentially contaminated medium is subjected to heating. The coupling device which may be conceived of as a receptacle is made of plastic that is substantially transparent (transmissive) to microwave radiation.

Equipment capable of heating and disinfecting receptacles can be operated by means of the methods described above. This is comparatively unproblematic when the shape, dimensions, material, etc. of the receptacles and media are known. However, the composition of plastics may vary between different batches or from one supplier to another. Receptacles from different suppliers may also be composed of different materials. But in order to guarantee safe heating of the entire medium, the influences of materials on the heating process and possibly different configurations of the receptacles must be taken into account.

Thus medical personnel are faced with the substantial problem of knowing or finding out what material the receptacle currently in use is made of.

It is the object of the invention to suggest an improved method for heating volumes of media in a closed receptacle by means of an electromagnetic radiation, which method can be used for a variety of receptacles having different thermodynamic characteristics. The invention has the further object of suggesting an apparatus for implementing the method.

SUMMARY OF THE INVENTION

The present invention provides a method for heating volumes of media in a closed receptacle by means of an electromagnetic radiation, wherein a database is established prior to carrying out heating in that in a step A at least one reference receptacle which is made of a known material, has a known volume and contains a known medium is irradiated in each instance by a first to nth radiation for a period of time, wherein the characteristics of the first to nth radiation are known, in a step B a number of measurement values of at least one measured quantity are collected at known measurement times over the duration of the irradiation and acquired as measurement sequences associated with the reference receptacle and are stored retrievably as reference measurement sequences, in a step C those reference measurement sequences which were created within a selected irradiation period during which a selected amount of energy was coupled into the reference receptacle are selected from the reference measurement sequences, in a step D an irradiation regime is derived in each instance from the selected reference measurement sequences and is stored so as to be associated with these selected reference measurement sequences, and wherein when heating is carried out in a step a the receptacle is irradiated for a known irradiation period by the radiation having characteristics which are known, and at least one measurement value of a measured quantity, which measurement value is associated with the receptacle and is associated with a measurement time within the irradiation period, is collected and is checked for the presence of a match with the values of reference measurement sequences stored in a database, in a step b thereafter, when there is a match between the at least one measurement value and a value of a reference measurement sequence, an irradiation regime associated with the relevant reference measurement sequence is selected, and in a step c thereafter, the heating of the receptacle is continued using the selected irradiation regime until a predetermined end point temperature.

The invention proposes a possibility by which a heating of the medium in the receptacle can be carried out without the need for a user of the method to have exact knowledge of the characteristics of the receptacle. Accordingly, for example, the receptacle can be a Luer® connector (or Luer® Lock) holding a medium in which a bacterial count possibly contained therein is to be reduced by heating.

The heating of the medium is not carried out under flow conditions. A volume of the medium is enclosed in an interior of the receptacle or reference receptacle, preferably without bubbles, for the duration during which steps A to D and steps a to c are carried out.

It is generally sufficient to carry out steps A to D one time before first using the method according to the invention. Steps a to c can be repeated as often as necessary. While steps a to c are being carried out, the measurement values, reference measurement sequences and irradiation regimes collected in steps B to D can be supplemented and/or corrected and new measurement values, reference measurement sequences and irradiation regimes can be added to the database.

By measured quantities is meant physical quantities such as, e.g., temperature, time, magnitude of electromagnetic radiation, phase of electromagnetic radiation and frequency of electromagnetic radiation. It has proven advantageous when one or more measured quantities are selected from the measured quantities and derived measured quantities are then formed from these selected measured quantities and used as measurement values of the reference measurement sequences in step a and as measurement values in step B. It is particularly advantageous when the real part and/or imaginary part of the permittivity are/is used as derived measured quantity.

A first electromagnetic radiation (also referred to as first radiation for the sake of simplicity) is a radiation which is suitable for heating the medium, e.g., microwave radiation, having known characteristics, e.g., a first wavelength, a first phase or a first power. Each of the first to nth radiations differs in at least one characteristic from the other radiations.

A reference measurement sequence is created based on the measurement values determined in step B. In this respect, a function can be derived from the reference measurement sequence by which to approximate the reference measurement sequence. An approximation of this kind can be carried out by means of regression methods known to the person skilled in the art.

In an advantageous embodiment of the method according to the invention, it is possible that for creation of the reference measurement sequences the temperature of the medium is acquired by means of a sensor and an acquired temperature is stored so as to be associated with the outer wall of the reference receptacle. In this way, a correlation is made between the temperatures of the outer wall and the medium. This makes it possible in an advantageous manner to draw conclusions about the temperature of the medium solely from the temperature of the outer wall while carrying out the method.

A function of this kind is obtained, for example, through a regression curve of a quantity of measurement values at various measuring times and/or at various locations. Further, various confidence intervals, e.g., 90%, 95% or 99% (confidence limits), can be calculated for a regression curve of this kind by means of various known methods as is broadly known to the person skilled in the art from the field of descriptive statistics and metrology. At a 95% confidence interval, for example, 95% of all of the confidence intervals that can be calculated from the function values lie within the 95% confidence interval.

In further embodiments of the method according to the invention, the confidence intervals within the meaning of the present description can also be set arbitrarily. Further, they can be estimated or calculated based on a rule that deviates from the above-stated definition of a confidence interval.

It will be assumed in the following that a concrete definition of the confidence interval is determined is each instance for implementing a determined embodiment of the method according to the invention.

A measurement value acquired in step a preferably matches a reference measurement sequence when this measurement value lies within the confidence interval of this reference measurement sequence.

An irradiation regime can be derived from the function determined in the above manner. In the simplest case, the derived irradiation regime is made up of an irradiation period and a radiation on the basis of which the relevant reference measurement sequence and subsequently the function thereof were obtained. It is also possible that an irradiation regime, although derived from a reference measurement sequence or the regression curve or function thereof, does not match or does not completely match the irradiation regime (irradiation period and radiation) which led to the reference measurement sequence.

An irradiation regime indicates the parameters, e.g., radiated power of the electromagnetic radiation, duration of irradiation (irradiation period) of the reference receptacle or receptacle and, where applicable, changes in characteristics of the electromagnetic radiation such as emitted power, wavelength and/or phase over the irradiation period, with which an irradiation and, therefore, a heating of the receptacle takes place. The aim is to introduce a predetermined amount of energy into the medium by means of a selected irradiation regime and to bring the temperature of the medium to a required temperature (reference temperature, end point temperature) dependably and throughout the medium. Any possible startup times, for example between an actuation of a radiation source and the emission of the electromagnetic radiation, are preferably taken into account in the irradiation regime.

An irradiation regime may be illustrated, for example, by a diagram having time as function range and the temperature of the medium on the one hand and values of a characteristic of the radiation (e.g., power, frequency, wavelength) on the other hand as value ranges. The measurement values of the temperatures plotted over time give the reference measurement sequence. The characteristic of radiation over time gives the irradiation regime which led to the depicted reference measurement sequence. Of course, a depiction of this kind can be multidimensional, for example when a plurality of characteristics of the radiation change over time.

Further, an irradiation regime can be derived from a known function, for example a regression of a reference measurement sequence, which has been interpolated and/or extrapolated. It is also possible for a function of a reference measurement sequence that is determined or estimated based on measurement values of step B to be transformed, for example linearized. Confidence intervals in the form of allowable classes or class widths can be defined for transformed functions, for example.

By "reflectivity" is meant hereinafter the portion of an electromagnetic radiation (hereinafter "radiation" for the sake of brevity) which is directed to a body (for example, a measured body) and reflected at a surface of the body.

Correspondingly, by "transmissivity" is meant the portion of the electromagnetic radiation which penetrates through the body or measured body (transmitted radiation). The electromagnetic radiation can be altered when penetrating the body. For example, the phase and frequency or frequency band of the transmitted radiation can be altered.

"Permittivity" describes the permeability of a material to electromagnetic fields. Permittivity is temperature-dependent and/or frequency-dependent. Dielectric losses of the electromagnetic radiation in the material can be indicated by the imaginary part of the permittivity, while the capability of the material to pass an electromagnetic field is described by the real part. If the permittivity has both a real part and an imaginary part, the frequency-dependent phase shift can be determined.

When the electromagnetic radiation passes through a medium, e.g., a body, a liquid, a suspension or a dispersion, the phase of the electromagnetic radiation can be shifted in a frequency-dependent manner. A frequency-dependent phase shift of this kind occurs when dielectric losses are also caused through the material such that the permittivity of the material is to be described by a real part and an imaginary part.

The end point temperature is a temperature such that, when it is reached, the medium has a required temperature, namely throughout the medium. Accordingly, there should be no areas in the medium where the required temperature of the medium is not reached. Further, this required temperature is to be maintained over a sufficiently long time period of, e.g., 5, 10, 15, 20, 25, 30 seconds or more than 30 seconds.

The reference receptacle is made of a known material which preferably as regards the heating behavior thereof when irradiated with the electromagnetic radiation has the same characteristics as a material from which the receptacle is expectedly made. The volume and the shape of an interior space of the reference receptacle are also known and are the same as or similar to the expected volume and shape of an interior space of a receptacle. The outer dimensions and wall thickness of the reference receptacle are preferably also known and are the same as or similar to the corresponding dimensions of the receptacle. The known medium in the reference receptacle and the medium to be heated in the receptacle are preferably the same. If it is not possible to use an identical medium, the media should be as similar to each other as possible, particularly with respect to the heating behavior of the media and the absorption behavior of the first to nth radiation.

While the method according to the invention is being carried out, it is possible to collect further measurement values during heating and to check for a match between at least a selection of the further measurement values and values of that reference measurement sequence (hereinafter also referred to as selected reference measurement sequence) with which the selected irradiation regime is associated. A match can also be present when individual further measurement values do not lie in the confidence interval but a regression curve of the further measurement values lies within the confidence interval.

This type of configuration of the method according to the invention advantageously affords the possibility of monitoring whether or not the selection of irradiation regime is actually appropriate. For example, when the selection of an irradiation regime is made on the basis of an individual measurement value or on the basis of measurement values that were determined within a short time period, it can be checked based on further measurement values whether or not the same selection would also be made with the further measurement values.

In a further embodiment of the method according to the invention, if no match is determined, another irradiation regime is selected and the heating is continued with the selected other irradiation regime. This procedure is particularly important when it is determined based on further measurement values that these further measurement values do not lie within the confidence interval of the reference measurement sequence. If the further measurement values lie in the confidence interval of another reference measurement sequence, for example, the irradiation regime that is associated with this other reference measurement sequence is selected and used further.

In a possible embodiment of the method, an irradiation regime composed of the two above-mentioned irradiation regimes is created and stored. Alternatively, a new irradiation regime can be determined based on the two relevant reference measurement sequences. If the further measurement values are associated with the confidence intervals of a plurality of reference measurement sequences, the above applies in a corresponding manner.

It is also possible that when no match is determined between the further measurement values and the confidence interval of the first reference measurement sequence used, the heating is terminated and an error signal is generated. The error signal can also be generated when there is no other irradiation regime that can be selected. The error signal can be visual and/or audible. In a further embodiment of the method, the generation of an error signal can be documented.

Further, the method according to the invention can be configured in such a way that in the absence of a match of at least one further measurement value based on the further measurement values acquired up to that point, a predicted irradiation regime is calculated and the heating is continued with the predicted irradiation regime. When the method is configured in this way, the predicted irradiation regime is not tied to the presence of a reference measurement sequence. However, rules for calculating the predicted irradiation regime can be derived from the database and from the reference measurement sequences, confidence intervals and irradiation regimes stored therein.

The predicted irradiation regime can be adopted in the database and stored so as to be repeatedly retrievable. The predicted irradiation regime can be taken into account for further calculations of predicted irradiation regime (self-learning database).

A measured quantity can be selected from a reflectivity of the receptacle, a transmissivity of the receptacle, at least one temperature at at least one selected point or area of the receptacle, or a frequency-dependent phase shift of a portion of the radiation penetrating the receptacle.

In further configurations of the method, at least two measured quantities can also be selected from a group of measured quantities comprising a reflectivity, a transmissivity, a temperature and a phase shift of the radiation.

The method according to the invention can be used in an extremely advantageous manner for disinfecting the interior of the receptacle. In this regard, the receptacle is preferably a medical device or a component of a medical device. In a preferred use of the method, the receptacle is a Luer® connector (Luer® Lock).

The present invention further provides an apparatus for heating volumes of media in a closed receptacle by means of an electromagnetic radiation. The apparatus has a radiation source for providing an electromagnetic radiation, a measurement space for receiving the receptacle, and an emitting device for directed emission of the radiation into the measurement space, and a regulating-and-control unit for regulating and controlling the supply and emission of the radiation corresponding to an irradiation regime, and is characterized in that the regulating-and-controlling unit is connected to at least one sensor and the at least one sensor is configured to acquire at least one measurement value of a measured quantity, which measurement value is associated with the receptacle, the regulating-and-controlling unit is in communicative connection with a storage unit in which a quantity of reference measurement sequences and a quantity of irradiation regimes associated with the reference measurement sequences are stored as a database, and the regulating-and-controlling unit has a checking unit which checks for a match between the at least one acquired measurement value and a value of the reference measurement sequences and which associates an irradiation regime with the acquired, checked measurement value when a match is established.

In order to prevent radiation exiting unintentionally from the measurement space, the latter is preferably constructed in a closed manner. It can comprise multiple parts, e.g., can be folded up, and is preferably closed when heating is carried out.

The regulating-and-controlling unit of the apparatus according to the invention preferably has an extrapolation unit for deriving irradiation regimes from a quantity of measurement values.

The sensor is advantageously a sensor for acquiring at least a reflectivity of the receptacle (reflectivity sensor). A sensor of this type can be, for example, a radiation sensor such as a photodiode, a CCD sensor, a photomultiplier or a photocell.

Further, the sensor can be a sensor for acquiring at least a frequency-dependent phase shift of a portion of radiation penetrating the receptacle. Further, the sensor can be a sensor for acquiring a transmissivity of the electromagnetic radiation. The frequency-dependent phase shift and the transmissivity can also both be acquired at the same time by a correspondingly constructed sensor.

The sensor for acquiring at least a frequency-dependent phase shift can be provided in addition to the radiation sensor (permittivity sensor). The functions of the radiation sensor and the sensor for acquiring at least a frequency-dependent phase shift can also be performed by one sensor.

In a further embodiment of the apparatus according to the invention, the sensor is a sensor for acquiring a temperature of the receptacle (temperature sensor). A sensor of this type can be arranged as a probe directly in an interior space of the receptacle. It can directly contact the medium. The sensor can also communicate with the surface of the receptacle and in this way can allow a surface temperature of the receptacle to be acquired.

In a further embodiment, the sensor can be formed to acquire a transmissivity (transmissivity sensor).

The various embodiments and arrangements of the sensors can be combined.

The radiation source preferably has an emitting device for emitting the radiation. The emitting device is preferably at least one antenna, but can also be at least one waveguide or at least one other input-coupling structure, for example. The shape, dimensioning and relative arrangement of the emitting device is adapted to the irradiation regime or irradiation regimes to be applied.

The apparatus according to the invention preferably has a frame through which the elements of the apparatus are held and positioned relative to one another. In addition, a shielding of the electromagnetic radiation can be achieved by means of the frame so that an environment of the apparatus is not exposed to unnecessary loading by the electromagnetic radiation.

The apparatus according to the invention can be configured as a stationary device or can be a component part of a stationary device. However, it is preferable to use the apparatus according to the invention in a device which can be brought to the place of use by the user in a simple manner. The apparatus is preferably arranged in a hand-held device and can be moved by a user to the receptacle with the medium to be heated and used to heat the medium.

The method according to the invention and the apparatus according to the invention are preferably configured and constructed in such a way that international standards requirements, particularly requirements of the International Pharmacopoeia standard, are met. Stricter national or regional requirements are preferably complied with through the choice of implementation and configuration of the method and through the choice of configuration of the apparatus.

BRIEF DESCRIPTION OF THE DRAWINGS

The invention will be described more fully in the following with reference to embodiment examples and drawings. The drawings show.

In all of the drawings, identical reference numerals denote identical components.

DETAILED DESCRIPTION OF THE PRESENT INVENTION

Figure 1:
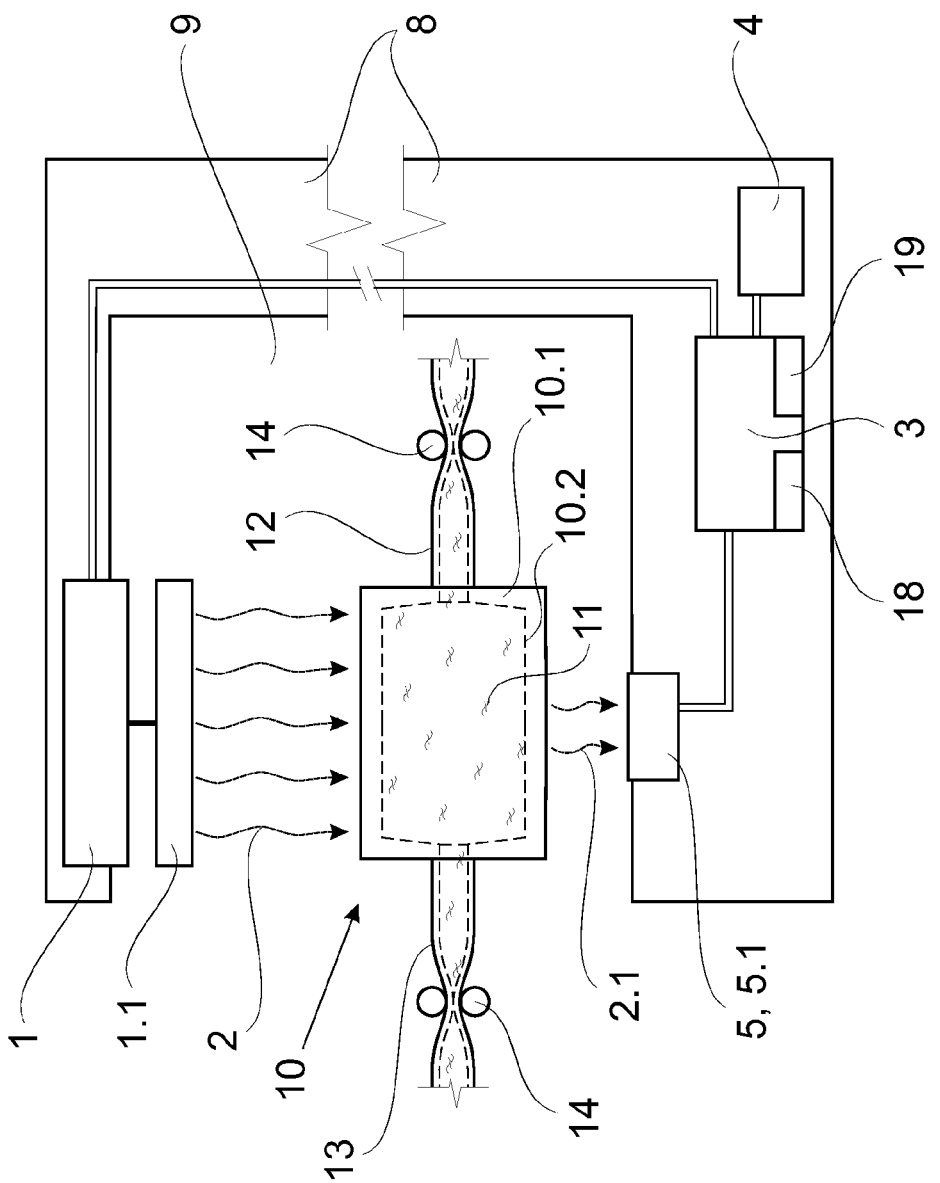
FIG. 1 a schematic layout of a first embodiment example of an apparatus according to the invention.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawing making apparent to those of skill in the art how the several forms of the present invention may be embodied in practice.

The essential elements of an apparatus according to the invention include a radiation source 1 for generating and providing an electromagnetic radiation 2, an emitting device 1.1 for emitting the electromagnetic radiation 2, at least one sensor 5, a regulating-and-controlling unit 3 and a database 4 (FIG. 1).

A first embodiment example of an apparatus according to the invention, as is shown in FIG. 1, has a frame 8 at which the radiation source 1, the emitting device 1.1 and a sensor 5 designed to acquire a permittivity of the electromagnetic radiation 2 (hereinafter permittivity sensor 5.1) are held and positioned relative to one another in a predetermined manner. The frame 8 is part of a housing of a device (not shown). In further embodiments of the apparatus, the frame 8 can also be formed independent from a housing or a device. A portion of the frame 8 encloses a measurement space 9 in which a receptacle 10 that can also be a reference receptacle 10 can be arranged for carrying out the heating of a medium 11 in the receptacle 10. The radiation source 1 is connected to the emitting device 1.1 by means of which the electromagnetic radiation 2 supplied by the radiation source 1 is directed from one side of the measurement space 9 and can be radiated into the measurement space 9. Opposite the emitting device 1.1 on the other side of the measurement space 9, the permittivity sensor 5.1 is arranged in such a way that at least a fraction of a transmitted electromagnetic radiation 2.1 impinges at least partially on the permittivity sensor 5.1. The transmitted electromagnetic radiation 2.1 is that portion of the electromagnetic radiation 2 which penetrates the receptacle 10 arranged in the measurement space 9.

The radiation source 1 and the permittivity sensor 5.1 are signal-connected to the regulating-and-controlling unit 3. The regulating-and-controlling unit 3 is connected in turn to the database 4. The database 4 is a calculator-and-storage unit in which data can be filed, stored and retrieved again. The connection between the regulating-and-controlling unit 3 and database 4 is realized by means of a cable connection as data line. In further embodiments of the apparatus, the data line can also be realized wirelessly, for example, by radio or optically. The regulating-and-controlling unit 3 has an extrapolation unit 18 for extrapolating reference measurement sequences 16 and irradiation regimes and a checking unit 19 to check for matches between measurement values 15 and confidence intervals 17 (see also FIGS. 4 to 7).

The receptacle 10 is made from a material which is transmissive to the electromagnetic radiation 2. It has a receptacle wall 10.1 enclosing an interior space 10.2 of the receptacle 10. The medium 11 can be guided into the interior space 10.2 via an inlet line 12 and guided out of the interior space 10.2 via an outlet line 13. The inlet line 12 and outlet line 13 have in each instance a closure 14 operative to close the inlet line 12 and the outlet line 13. In a further embodiment of the apparatus, the closures 14 can communicate with the regulating-and-controlling unit 3 and be opened and closed by the latter by means of a closure unit (not shown).

Figure 2:
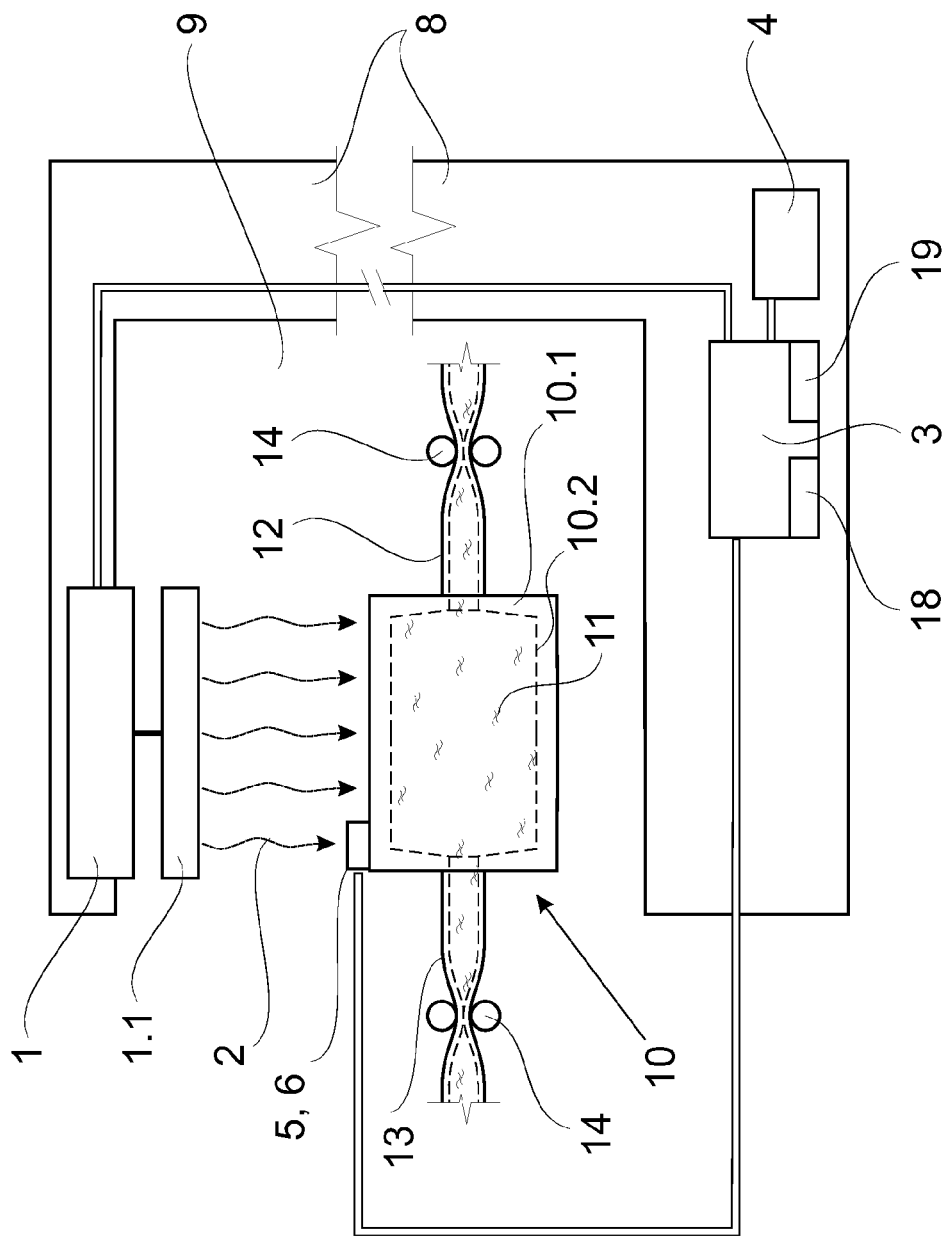
FIG. 2 a schematic layout of a second embodiment example of an apparatus according to the invention.

FIG. 2 shows a second embodiment example of the apparatus according to the invention in which a sensor 5 which is designed to acquire temperatures of the medium 11 in the interior space 10.2 of the receptacle 10 (hereinafter referred to as temperature sensor 6) is arranged instead of the permittivity sensor 5.1. The temperature sensor 6 is arranged externally at the receptacle wall 10.1 and is connected to the regulating-and-controlling unit 3. In further embodiments, the temperature sensor 6 can also be arranged in the interior space 10.2. Combinations of the arrangement of the sensors 5 are also possible.

Figure 3:
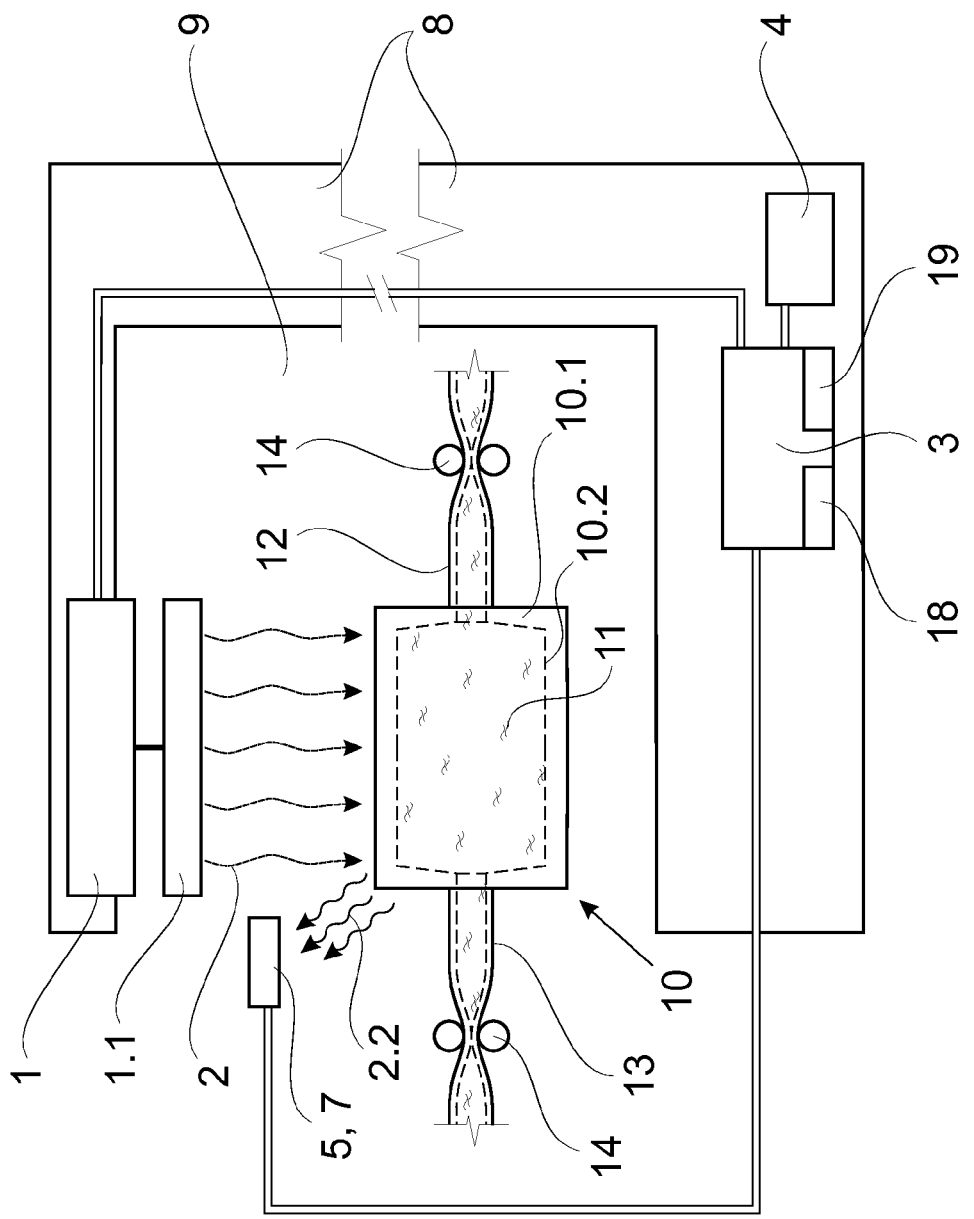
FIG. 3 a schematic layout of a third embodiment example of an apparatus according to the invention.

In a third embodiment example according to FIG. 3, instead of the permittivity sensor 5.1 or temperature sensor 6, a sensor 5 is arranged which is designed to acquire a reflected electromagnetic radiation 2.2 and is referred to as reflectivity sensor 7. The reflected electromagnetic radiation 2.2 is that fraction of the electromagnetic radiation 2 radiated into the interior space 10.2 that is reflected by the material and by the surface of the receptacle 10. Reflections can occur at boundary surfaces of the material and at structures in the material.

Figure 4:
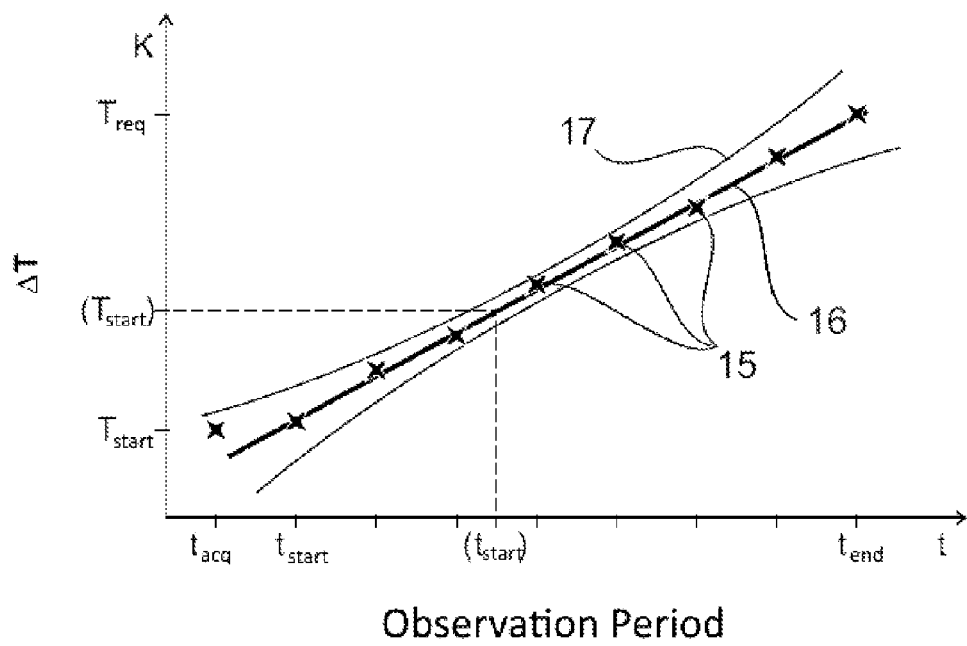
FIG. 4 a schematic depiction of a reference measurement sequence with a confidence interval represented in a graph with time on the abscissa axis and temperature of a medium to be heated on the ordinate axis.

The relationship between reference measurement sequences 16 and irradiation regimes will be explained with reference to FIG. 4 by a simplified example of an apparatus with temperature sensor 6 (see also FIG. 2).

To obtain a reference measurement sequence 16, a reference receptacle 10 is inserted into the measurement space 9 before carrying out heating of the medium 11. The reference receptacle 10 has inner and outer dimensions and material corresponding to a receptacle 10 which is expected to be used in practice and which is therefore provided with the same reference numeral. A medium 11 which corresponds as far as possible to or is identical to the medium expected to be used in practice is provided in the reference receptacle 10.

An electromagnetic radiation 2 is generated by the radiation source 1 and is emitted into the interior space 10.2 and onto the reference receptacle 10 through the emitting device 1.1. The characteristics of the electromagnetic radiation 2 such as frequency, phase and power are known. At the start of heating, i.e., at start time $t_{start}$, the temperature of the outer wall of the reference receptacle 10 is acquired by the temperature sensor 6 as a first measurement value 15. To create the reference measurement sequences 16, the temperature of the medium 11 is further acquired by a sensor, not shown here, and is stored so as to be associated with an outside temperature of the receptacle wall 10.1 of the reference receptacle 10. In this way, a correlation is detected between the temperatures of the receptacle wall 10.1 and the medium 11. In an advantageous manner, this makes it possible to deduce the temperature of the medium 11 while carrying out the method solely from the temperature of the receptacle wall 10.1. The temperatures are then acquired at regular measuring times over the duration of irradiation as respective measurement values 15 and are stored so as to be associated with the measuring times. The heating is concluded when an end point temperature $T_{req\ (required)}$ is reached in that the radiation source 1 is actuated and switched off by the regulating-and-controlling unit 3. An energy has been introduced into the medium 11 by the electromagnetic radiation 2 which leads to a temperature value of the end point temperature $T_{req}$ for heating the medium 11.

In further embodiments of the method according to the invention, the radiation source 1 can be actuated in such way that the energy transmitted through the electromagnetic radiation 2 is reduced and the temperature of the end point temperature $T_{req}$ is maintained in the medium 11 over a determined time period.

The irradiation period required for heating the medium 11 by means of the electromagnetic radiation 2 having the known characteristics is determined and the reference measurement sequence 16 is stored in a correlated manner. The reference measurement sequence 16 is given by the measurement values 15. A function of the reference measurement sequence 16 (indicated by solid line) is derived based on the measurement values 15. A confidence interval 17 is calculated and stored for this function, the manner in which the confidence interval 17 is calculated being determined beforehand. In the example, the confidence interval 17 is calculated by taking into account the known measurement errors of the temperature sensor 6 and the device-related tolerances in generating, supplying and emitting the electromagnetic radiation 2 and on the basis of a suitable probability distribution (e.g., Gaussian distribution, Weibull distribution, Poisson distribution, etc.).

In the example, the end point temperature $T_{req}$ is calculated exactly at the end of the irradiation period in the course of heating the medium 11. Accordingly, it is possible to use the function of the reference measurement sequence 16 as irradiation regime at the same time and to associate it with the reference measurement sequence 16 and store it.

Reference measurement sequences 16, confidence intervals 17 and irradiation regimes of this type are determined to form the database 4 for a large number of reference receptacles 10 of different materials and/or different dimensions and for various media 11 and are stored in the database 4. Further, the characteristics of the electromagnetic radiation 2 are varied. These characteristics may be constant or changed linearly or nonlinearly over the irradiation period. Each variation of the electromagnetic radiation 2 is stored as one of first to nth electromagnetic radiation 2.

It is possible to determine the data of the database 4 for each individual apparatus. However, it is more advantageous when data which is already known beforehand is stored in the database 4. These data can be supplemented and/or corrected by specific data of the respective apparatus.

When carrying out the method according to the invention, instead of the reference receptacle 10, a receptacle 10 with a medium 11 is arranged in the measurement space 9. The temperature of the medium 11 is acquired first and is sent to the regulating-and-controlling unit 3 as starting temperature $T_{start}$. The acquired starting temperature $T_{start}$ is compared with starting temperatures $T_{start}$ stored in the database 4. The reference measurement sequences 16 having an identical starting temperature $T_{start}$ are pre-selected. In so doing, the reference measurement sequences 16 which contain within their confidence interval 17 a temperature value equal to the acquired starting temperature $T_{start}$ are also preselected. The reference measurement sequence 16 whose function contains the value of the acquired starting temperature $T_{start}$ is selected in the example shown here. The irradiation regime associated with the selected reference measurement sequence 16 is likewise selected. The radiation source 1 is actuated by the regulating-and-controlling unit 3 to heat the medium 11 corresponding to this selected irradiation regime. Since the regulating-and-controlling units 3 and databases 4 used at present allow very short times for the described temperature acquisition, selection of reference measurement sequence 16 and actuation of radiation source 1, these steps can be carried out at the start of the irradiation period.

In further embodiments, it is possible that the temperature of the medium 11 takes place at an acquisition time $t_{acq}$ occurring before the start time $t_{start}$. The above-described steps of temperature acquisition and selection of the reference measurement sequence 16 are carried out before start time $t_{start}$. The heating starts at start time $t_{start}$ with the actuation of the radiation source 1 by the regulating-and-controlling unit 3.

At the start of heating, the radiation source 1 is actuated corresponding to the selected irradiation regime by the regulating-and-controlling unit 3. The electromagnetic radiation 2 is generated, supplied and emitted into the measurement space 9 via the emitting device 1.1. The heating of the medium 11 is carried out corresponding to the selected irradiation regime.

In a further embodiment of the method, the temperature of the medium 11 is acquired at known measuring times within the irradiation period so as to be associated with the measuring time as further measurement values 15 and the respective measurement value 15 is sent to the regulating-and-controlling unit 3, where checking is carried out as to whether or not the measurement value 15 occurs at the corresponding (measuring) time within the confidence interval 17 of the reference measurement sequence 16. If so, the heating is continued with the irradiation regime.

If checking shows that the further measurement value 15 does not lie within the confidence interval 17, an error signal is generated. In one embodiment, it is checked whether or not at least the further measurement value 15 following the deviating further measurement value 15 again lies within the confidence interval 17. If so, the heating is continued with the selected irradiation regime until the irradiation period is ended or the end point temperature $T_{req}$ is reached, depending on which criterion was selected for terminating heating.

In a further embodiment of the method, when at least one further measurement value 15 deviates from the confidence interval 17 the database 4 is searched by the regulating-and-controlling unit 3 in order to find another reference measurement sequence 16 and associated irradiation regime with which heating can continue. In so doing, the selection of the other reference measurement sequence 16 is carried out based on at least one further measurement value 15, but based on a plurality of further measurement values 15 in improved embodiments. In a further embodiment of the method, the reference measurement sequence 16 which is accordingly composed of the selected reference measurement sequence 16 and the other reference measurement sequence 16 is retrievably stored in the database 4.

Those embodiments of the method in which another measured quantity and/or a derived measured quantity are/is used are also carried out corresponding to the procedure mentioned above.

In further embodiments of the method according to the invention, a plurality of measured quantities and/or derived measured quantities can also be used (temperature, reflectivity, transmissivity, real part of permittivity and/or imaginary part of permittivity). By using a plurality of measured quantities and/or derived measured quantities, the selection of the reference measurement sequence 16 and associated irradiation regime is based on value triplets, value quadruplets, and so on, so as to improve certainty that the irradiation regime of the selected reference measurement sequence 16 can also be maintained over the entire irradiation period. Alternatively, a selection can be made based on a measured quantity or derived measured quantity and can be checked through the selection based on at least one further measured quantity or derived measured quantity.

In an alternative procedure for steps A to D, the heating can also be terminated when the irradiation period expires. In this case, it is checked subsequently whether or not the end point temperature $T_{req}$ was reached within the irradiation period and at what time within the irradiation period this may have occurred. If the end point temperature $T_{req}$ is reached within the irradiation period, the reference measurement sequence 16 is selected. To avoid exceeding the end point temperature $T_{req}$, an irradiation regime associated with the reference measurement sequence 16 is configured such that the power of the emitted electromagnetic radiation 2 (emitted power) is reduced.

If the end point temperature $T_{req}$ is not reached within the irradiation period, the reference measurement sequence 16 is rejected. Alternatively, the reference measurement sequence 16 can be used as basis for determining (e.g., through extrapolation) an extrapolated irradiation regime.

Figure 5:
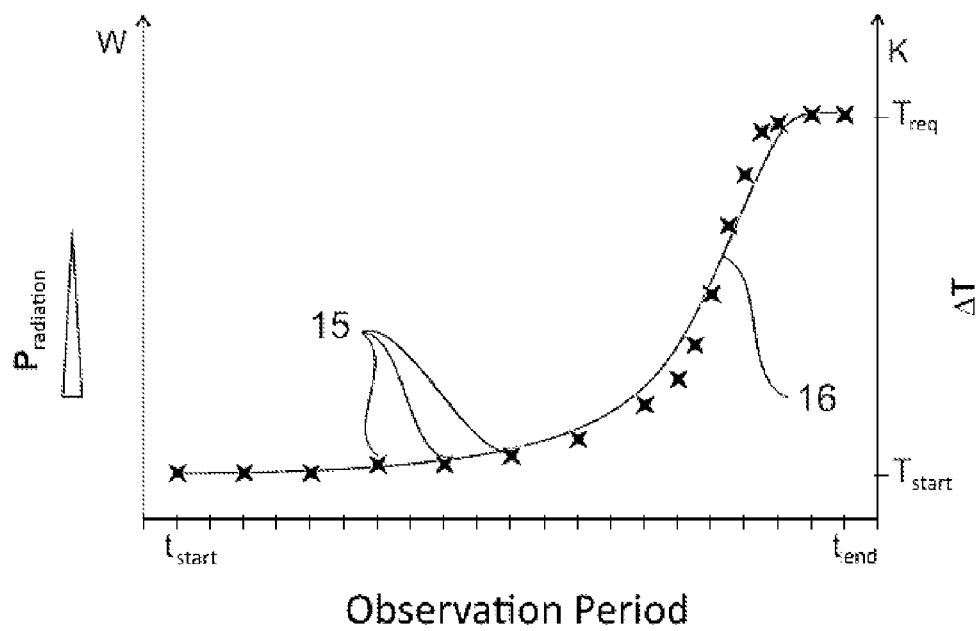
FIG. 5 a schematic depiction of an irradiation regime and a reference measurement sequence represented in a graph with time on the abscissa axis and radiation power and temperature of a medium to be heated as respective ordinates.

A further example of an irradiation regime and a reference measurement sequence 16 is shown in FIG. 5. The measurement values 15 of the reference measurement sequence 16 are indicated by crosses. The measurement values 15 of measured quantity temperature were acquired over the irradiation period (between start time $t_{start}$ and end time $t_{end}$) by means of a temperature sensor 6. At the same time, the power of the emitted electromagnetic radiation 2 was reduced over the irradiation period in a nonlinear manner (solid line). It will be noted that the temperature of the medium 11 initially rises only gradually in spite of the high power of the electromagnetic radiation 2. Around the start of the second half of the irradiation period, the temperature rises exponentially with time although the power of the electromagnetic radiation 2 is reduced. This can be attributed for example to temperature-dependent energy absorption of the medium 11 and/or of the material of the receptacle 10 and effects such as constructive or destructive interferences of the electromagnetic radiation 2. To avoid exceeding the end point temperature $T_{req}$, the power per time unit is reduced to an increasing extent toward the end of the irradiation period. The irradiation regime shown (power of radiation over time) is associated with the reference measurement sequence 16 shown (temperature over time) and both are stored in the database 4.

Figure 6:
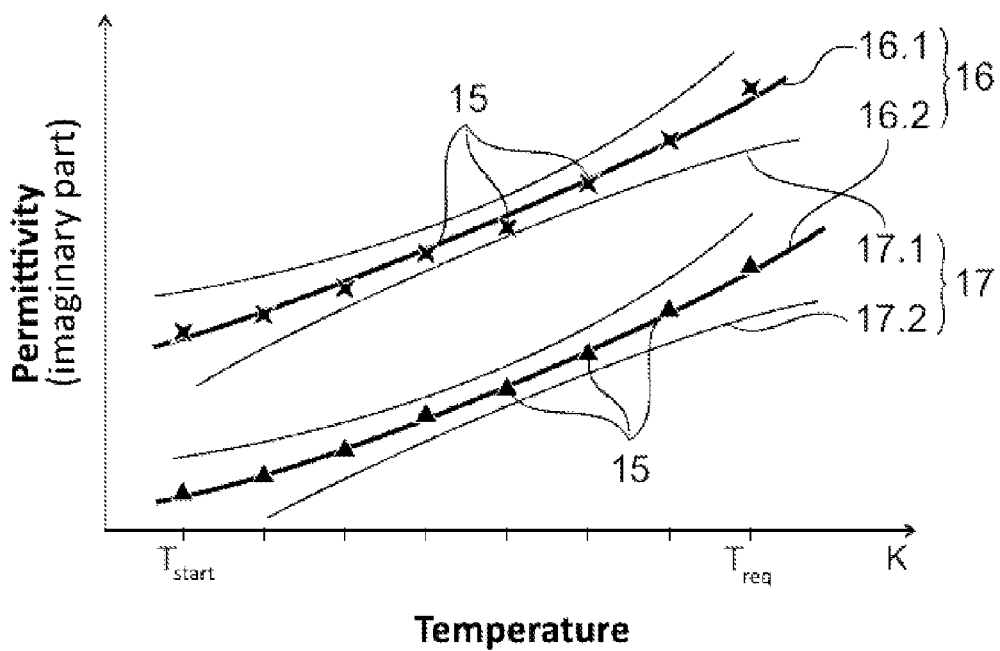
FIG. 6 a schematic depiction of reference measurement sequences of derived measured quantities, associated irradiation regimes and confidence intervals.

Two reference measurement sequences 16 with confidence intervals 17 are shown by way of example in a graph in FIG. 6. Temperatures are plotted in degrees Celsius on the abscissa axis. A starting temperature $T_{start}$ from which a heating of the medium 11 in the receptacle 10 commences and an end point temperature $T_{req}$ at which a required temperature of the medium 11 is reached are shown. The imaginary part of the acquired permittivity of the electromagnetic radiation 2 when penetrating the receptacle 10 filled with medium 11 is plotted on the ordinate axis. The imaginary part of the acquired permittivity is a derived measured quantity.

A first reference measurement sequence 16.1 is represented by a function which was derived from a regression of the measurement values 15 (represented by crosses) of the first reference measurement sequence 16.1. Based on the measurement values 15 and the function, a first confidence interval 17.1 of the function was calculated as 95% confidence interval 17. The first reference measurement sequence 16.1 has been determined through an irradiation of a medium 11 in the receptacle 10 by means of an electromagnetic radiation 2 of known wavelength and power. During the heating of the medium from the starting temperature $T_{start}$ to the end point temperature $T_{req}$, the permittivity has been acquired as measured quantity and the respective imaginary part thereof has been determined as derived measured quantity. It is assumed herein that the heating of the medium from the starting temperature $T_{start}$ to the end point temperature $T_{req}$ occurred within a specified irradiation period of 15 second.

The same also applies to a second reference measurement sequence 16. Through regression of the measurement value 15 (represented by triangles) of the second reference measurement sequence 16.2, a function and a second confidence interval 17.2 of the function are calculated as 95% confidence interval.

The first and second confidence intervals 17.1, 17.2 do not differ from one another over the depicted function range.

The first reference measurement sequence 16.1 was obtained through measurement values 15 which were acquired at a determined wavelength and power of the emitted electromagnetic radiation 2. The timing for introducing power into the medium 11 by means of the electromagnetic radiation 2 represents an irradiation regime. In a simple case, the characteristics of the electromagnetic radiation 2 were not altered over the irradiation period. However, as is shown by the curve of the first reference measurement sequence 16.1, the imaginary part of the permittivity increased nonlinearly with temperature.

Figure 7:
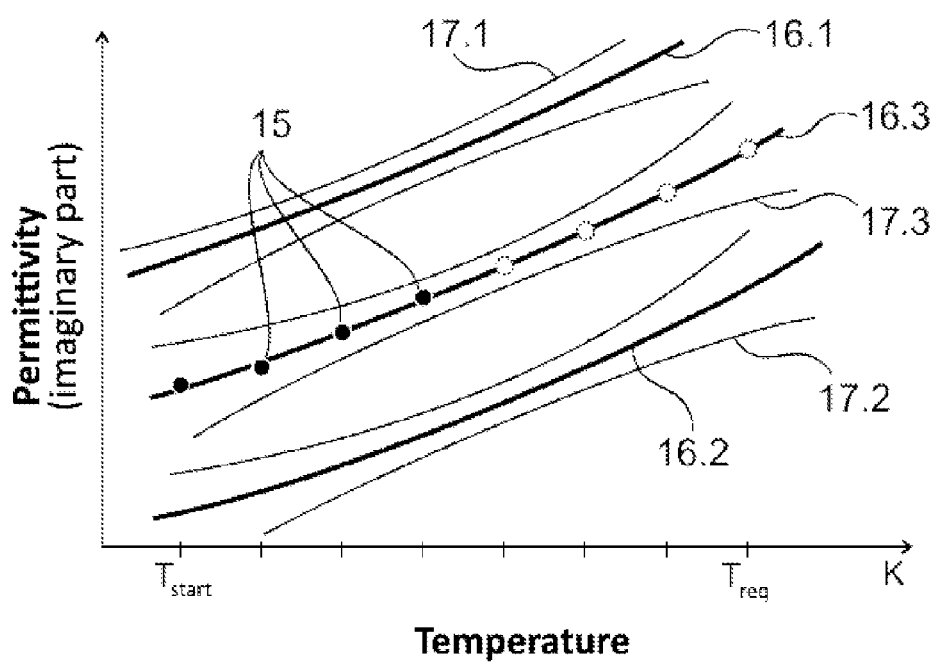
FIG. 7 a schematic depiction of measurement values of derived measured quantities and extrapolated irradiation regime.

A further embodiment of the method according to the invention is illustrated in FIG. 7. A first reference measurement sequence 16.1 with a first confidence interval 17.1 and a second reference measurement sequence 16.2 with a second confidence interval 17.2 are shown. A third reference measurement sequence 16.3 which is formed from only a few (four are shown) measurement values 15 is shown between the two reference measurement sequences 16.1, 16.2. Based on knowledge of the reference measurement sequences 16 stored in the database 4, the functions and confidence intervals 17 thereof and the irradiation regime, it is possible to extrapolate the curve of the third reference measurement sequence 16.3 until the end point temperature $T_{req}$ is reached proceeding from measurement values 15. The rest of the curve of the third reference measurement sequence 16.3, i.e., further imaginary measurement values 15 (indicated by dotted borders), is estimated based on known data. Subsequently, a third confidence interval 17.3 can be calculated in a known manner for the third reference measurement sequence 16.3 extrapolated in this way. Further, based on the third reference measurement sequence 16.3, a suitable irradiation regime can be predicted. The irradiation regime predicted in this way can be checked and, if necessary, corrected during application thereof by acquiring actual measurement values 15.

While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

REFERENCE NUMERALS 1 radiation source
1.1 emitting device
2 electromagnetic radiation
2.1 transmitted electromagnetic radiation
2.2 reflected electromagnetic radiation
3 regulating-and-controlling unit
4 database
5 sensor
5.1 permittivity sensor 6 temperature sensor
7 reflectivity sensor
8 frame
9 measurement space
10 receptacle, reference receptacle
10.1 receptacle wall
10.2 interior space
11 medium
12 inlet line
13 outlet line
14 closure
15 measurement values
16 reference measurement sequence
16.1 first reference measurement sequence
16.2 second reference measurement sequence
16.3 third reference measurement sequence
17 confidence interval
17.1 first confidence interval
17.2 second confidence interval
17.3 third confidence interval
18 extrapolation unit
19 checking unit

What is claimed is:

1. A method for heating volumes of media in a closed receptacle by electromagnetic radiation, wherein the method comprises, prior to carrying out heating, establishing a database by proceeding as follows:

irradiating in each instance at least one reference receptacle which is made of a known material, has a known volume and contains a known medium by a first to nth electromagnetic radiation for a period of time, the characteristics of the first to nth electromagnetic radiation being known, collecting a number of measurement values of at least one measured quantity at known measurement times over a duration of the irradiation and acquiring the measurement values as measurement sequences associated with the reference receptacle and storing them retrievably as reference measurement sequences, selecting from the collected reference measurement sequences those reference measurement sequences which were created within a selected irradiation period during which a selected amount of energy was coupled into the reference receptacle, deriving an irradiation regime in each instance from the selected reference measurement sequences and storing the irradiation regime so as to be associated with the selected reference measurement sequences; and wherein the method further comprises carrying out heating by proceeding as follows:

irradiating the receptacle for a known irradiation period by the electromagnetic radiation having characteristics which are known, and collecting at least one measurement value of a measured quantity, which measurement value is associated with the receptacle and is associated with a measurement time within the irradiation period, and checking the measurement value for the presence of a match with values of reference measurement sequences stored in a database, thereafter when there is a match between the at least one measurement value and a value of a reference measurement sequence, selecting an irradiation regime associated with the relevant reference measurement sequence, and then continuing the heating of the receptacle to a predetermined end point temperature $T_{req}$ using the selected irradiation regime.

2. The method of claim 1, wherein further measurement values are collected during heating and checking is carried out for a match between at least a selection of the further measurement values and values of that reference measurement sequence that is associated with the selected irradiation regime.

3. The method of claim 2, wherein if no match is determined, another irradiation regime is selected and heating is continued with the selected other irradiation regime.

4. The method of claim 3, wherein heating is terminated and an error signal is generated when no other irradiation regime can be selected.

5. The method of claim 2, wherein in the absence of a match of at least one further measurement value based on the further measurement values acquired up to that point, a predicted irradiation regime is calculated and heating is continued with the predicted irradiation regime.

6. The method of claim 5, wherein the predicted irradiation regime is adopted in the database and stored so as to be repeatedly retrievable.

7. The method of claim 1, wherein the at least one measured quantity is selected from a reflectivity of the receptacle, a transmissivity of the receptacle, at least one temperature at at least one selected point of the receptacle, or a frequency-dependent phase shift of a portion of the electromagnetic radiation penetrating the receptacle.

8. The method of claim 7, wherein at least two measured quantities are selected from a group of measured quantities which comprises a reflectivity, a transmissivity, a temperature and a phase shift of the electromagnetic radiation.

9. The method of claim 1, wherein the an interior of the receptacle is disinfected.

10. The method of claim 1, wherein the receptacle is a medical device or a component of a medical device.

11. The method of claim 1, wherein the at least one measured quantity comprises a reflectivity of the receptacle.

12. The method of claim 1, wherein the at least one measured quantity comprises a transmissivity of the receptacle.

13. The method of claim 1, wherein the at least one measured quantity comprises at least one temperature at at least one selected point of the receptacle.

14. The method of claim 1, wherein the at least one measured quantity comprises a frequency-dependent phase shift of a portion of the electromagnetic radiation penetrating the receptacle.

* * * * *